US009572703B2

(12) United States Patent
Matthews (10) Patent No.: US 9,572,703 B2
(45) Date of Patent: Feb. 21, 2017

(54) ORTHOTIC SOCK (75) Inventor: Martin Matthews, Redruth (GB)

(73) Assignee: DM ORTHOTICS LIMITED (GB)

(*) Notice: Subject to any disclaimer, the term of this patent is extended or adjusted under 35 U.S.C. 154(b) by 1307 days.

(21) Appl. No.: 13/375,671

(22) PCT Filed: Jun. 1, 2010

(86) PCT No.: PCT/GB2010/001063
§ 371 (c)(1),
(2), (4) Date: Dec. 1, 2011

(87) PCT Pub. No.: WO2010/139939
PCT Pub. Date: Dec. 9, 2010

(65) Prior Publication Data
US 2012/0071806 A1    Mar. 22, 2012

(30) Foreign Application Priority Data
Jun. 1, 2009  (GB) .................................. 0909459.0

(51) Int. Cl.
A61F 5/00        (2006.01)
A61F 5/01        (2006.01)

(52) U.S. Cl.
CPC ............ A61F 5/0111 (2013.01); A61F 5/0113 (2013.01); A61F 5/0127 (2013.01)

(58) Field of Classification Search
CPC ..... A61F 5/0111; A61F 5/0113; A61F 5/0127; A61F 5/0195; A61F 3/06; A61F 3/064; A61F 3/066; A61F 3/08; A61F 3/085; A43B 17/00; A43B 17/003; A43B 17/006; A43B 17/02; A43B 17/14; A61B 11/02; A61B 11/08; A61B 11/10; A41B 11/02; A41B 11/04; A41B 11/08; A41B 11/10
See application file for complete search history.

(56) References Cited

U.S. PATENT DOCUMENTS

| 4,811,727 | A | 3/1989 | Etienne | |
| 5,709,650 | A | 1/1998 | Colman | |
| 5,759,168 | A * | 6/1998 | Bussell et al. | 602/27 |
| 2006/0217649 | A1 * | 9/2006 | Rabe | 602/27 |
| 2007/0010773 | A1 * | 1/2007 | Watts | 602/27 |

(Continued)

FOREIGN PATENT DOCUMENTS

| DE | 10100039 | 7/2001 |
| DE | 20207156 | 8/2002 |

(Continued)

OTHER PUBLICATIONS

Matthews et al. "Effects of dynamic elastomeric fabric orthoses on children with cerebral palsy," Prosthetics and Orthotics International (2009) (00(0)), p. 1-9.

(Continued)

Primary Examiner — Kari Petrik
(74) Attorney, Agent, or Firm — Gardner Groff Greenwald & Villanueva, PC (57) ABSTRACT An orthotic sock for treatment of an orthopedic condition is formed from a resilient material and has means for restricting movement of a wearer's foot in one or more predetermined directions and/or means for assisting movement of a wearer's foot in one or more predetermined directions. An opening is defined through a posterior leg portion of the sock.

20 Claims, 5 Drawing Sheets (56) References Cited

U.S. PATENT DOCUMENTS

2011/0105973 A1* 5/2011 Watts .............................. 602/27

FOREIGN PATENT DOCUMENTS

| | | |
|---|---|---|
| DE | 202004007163 | 8/2004 |
| DE | 102004019007 | 11/2005 |
| FR | 2619709 | 3/1989 |
| GB | 2241647 | 9/1991 |
| GB | 2420716 | 7/2006 |
| JP | 09067701 | 3/1997 |
| JP | 2007332470 | 12/2007 |
| WO | 02051343 | 7/2002 |
| WO | 2005037139 | 4/2005 |
| WO | 2006045079 | 4/2006 |
| WO | 2008153675 | 12/2008 |

OTHER PUBLICATIONS

International Preliminary Report on Patentability dated Dec. 15, 2011 for international application No. PCT/GB2010/001063.

* cited by examiner

ORTHOTIC SOCK

CROSS-REFERENCE TO RELATED APPLICATION

This is a national-phase filing of PCT International Patent Application Serial No. PCT/GB2010/001063, filed Jun. 1, 2010, which claims the priority benefit of Great Britain Patent Application Serial No. 0909459.0, filed Jun. 1, 2009, both of which are hereby incorporated herein by reference.

TECHNICAL FIELD

The invention relates generally to an orthotic sock, and in particular to an orthotic sock for the relief or correction of an orthopaedic problem.

BACKGROUND

Various conditions exist that may inhibit an individual from moving their foot or ankle in a normal way. Such orthopaedic conditions may be congenital conditions or may be caused as a result of injury or misuse of the foot or ankle.

It is known to treat orthopaedic conditions of the foot and/or ankle by using suitable orthotic supports in the form of orthotic socks or stockings. Such orthotic supports are designed to relieve and/or correct the particular orthopaedic problem by various means including, both separately and in combination, the inhibition of movement of the ankle or foot in certain directions and the active assistance of movement of the ankle or foot in certain directions.

Figure 1:
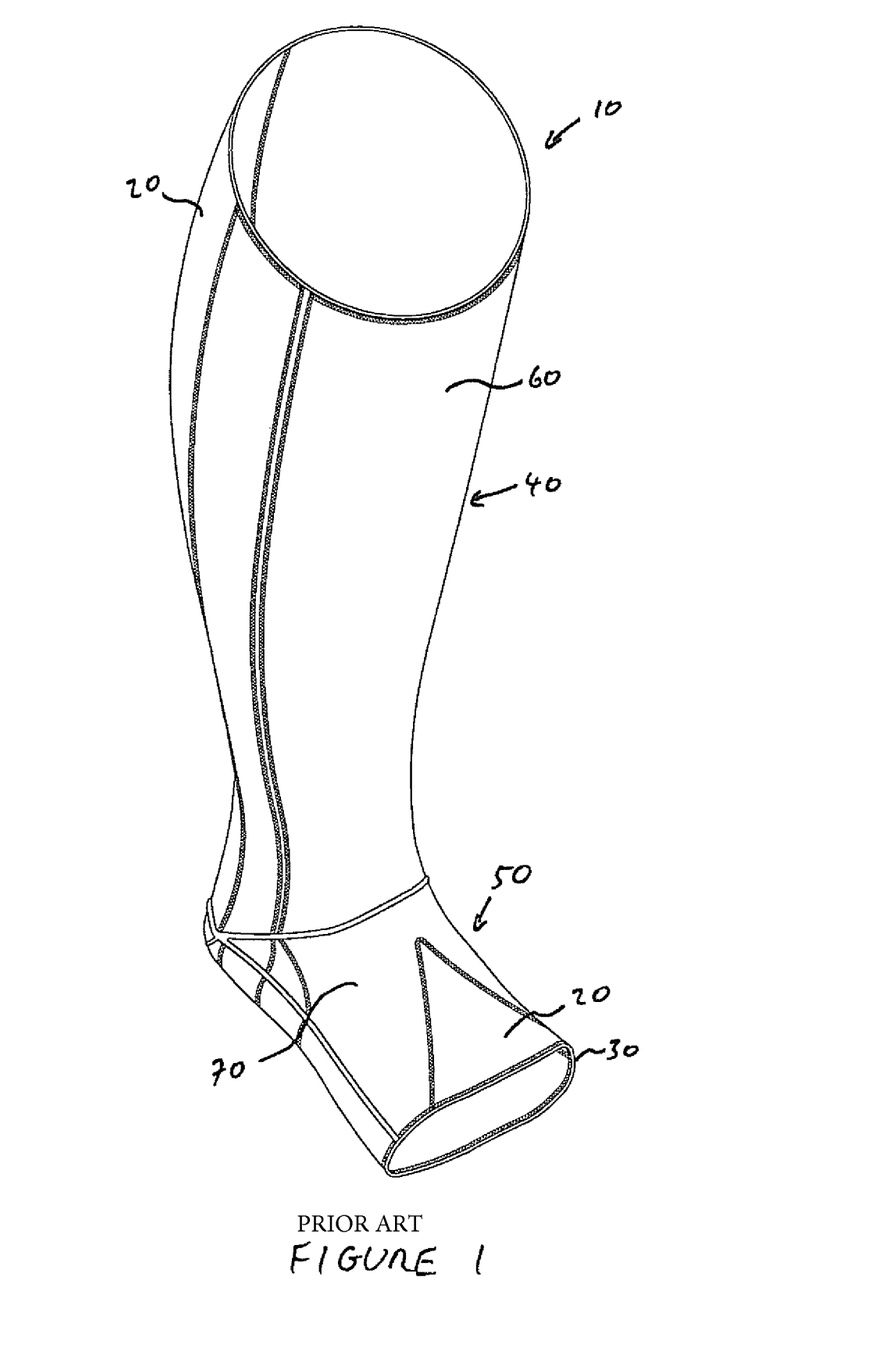
FIG. 1 is a perspective view of an orthotic sock of known configuration.
Figure 2A:
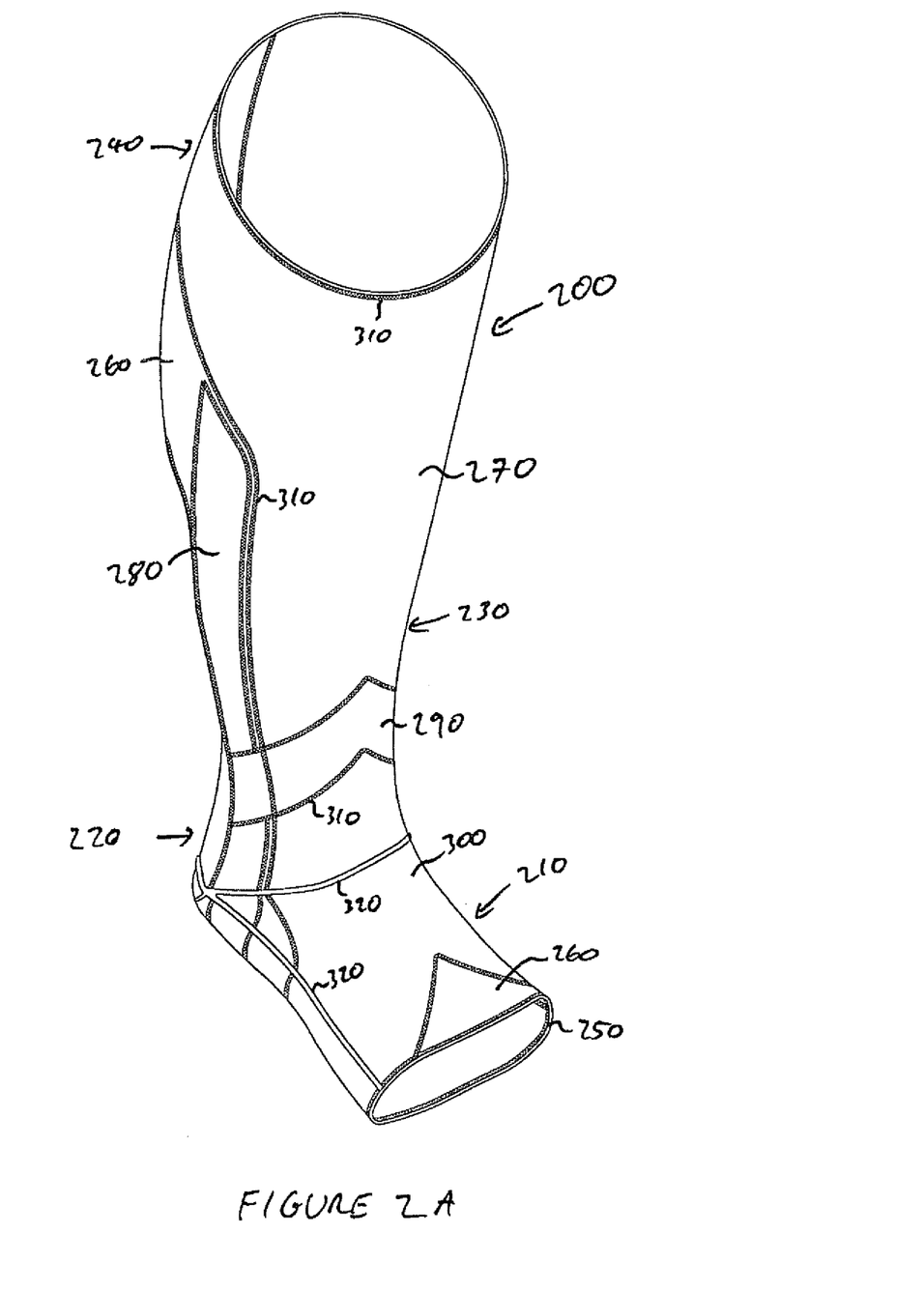
FIG. 2a is a perspective view of a sock according to a first aspect of the invention.
Figure 2B:
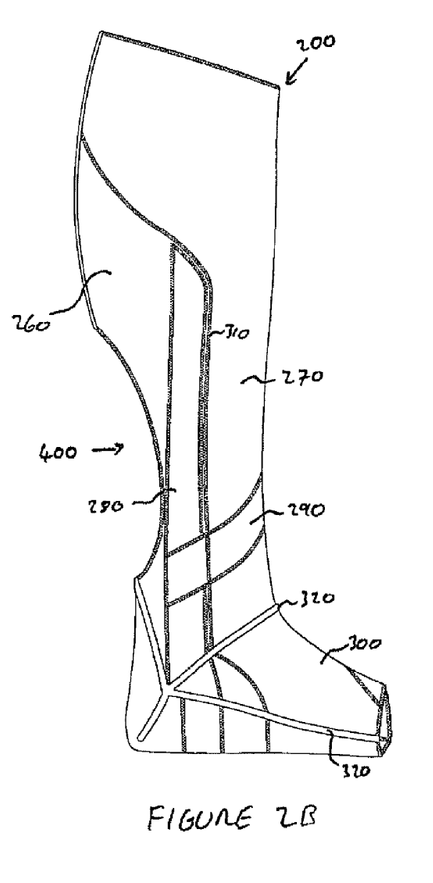
FIGS. 2b and 2c illustrate side projections of a sock according to the first aspect of the invention.
Figure 2C:
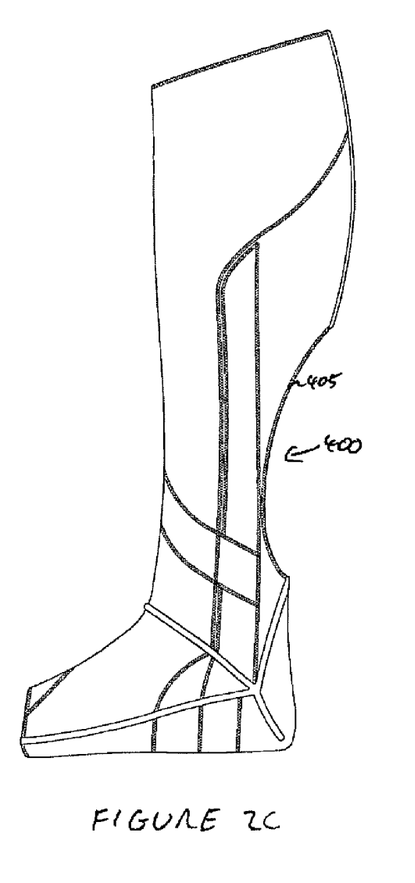
Figure 3A:
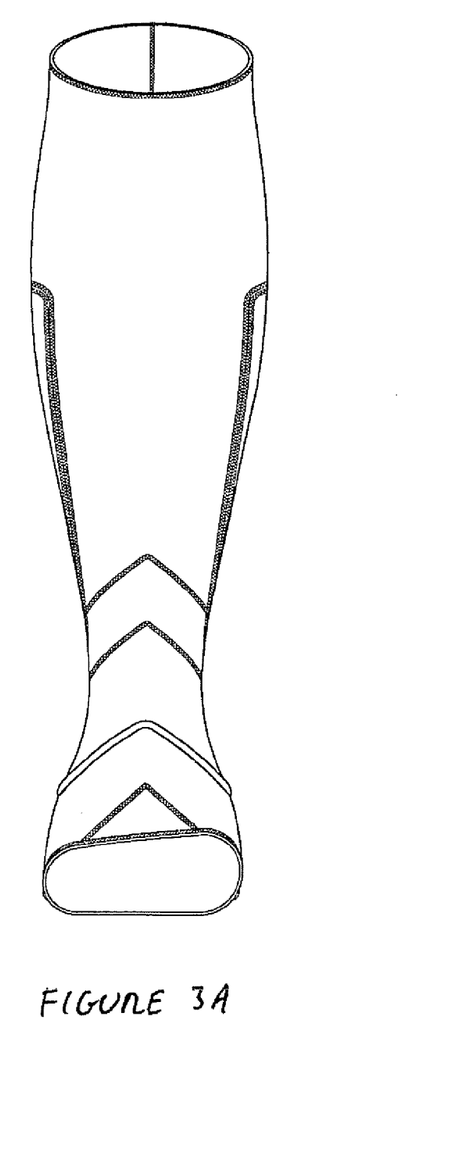
FIGS. 3a and 3b illustrate front and rear projections of a sock according to the first aspect of the invention.
Figure 3B:
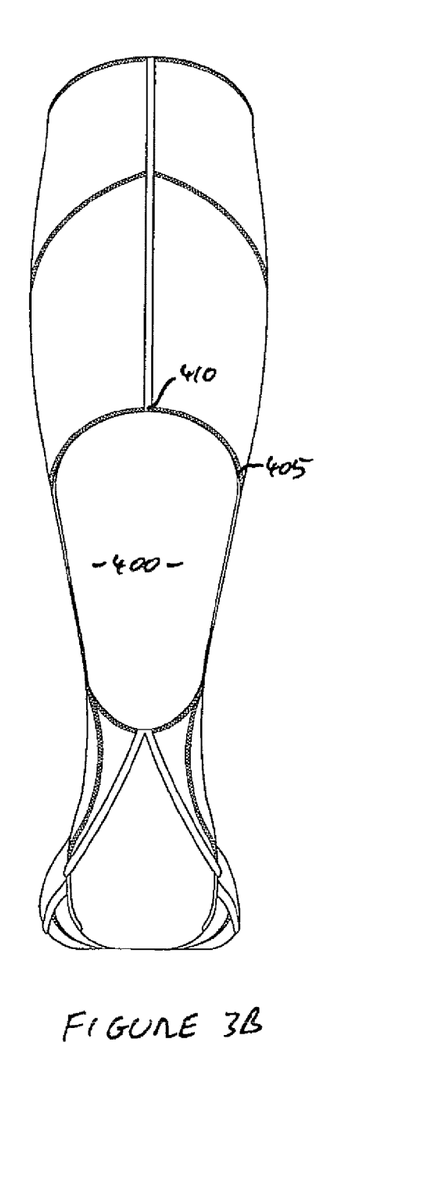
Figure 4A:
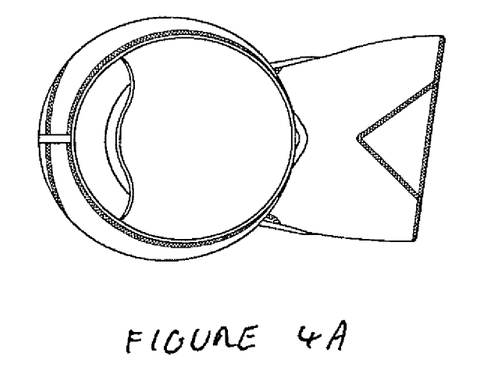
FIGS. 4a and 4b illustrate top and bottom projections of the sock according to the first aspect of the invention.
Figure 4B:
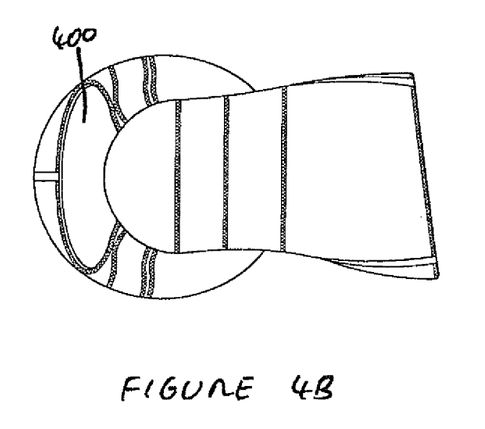

FIG. 1 illustrates a type of orthotic sock or stocking 10 for increasing dorsiflexion of a wearer's foot. Such a sock may be used to treat conditions that inhibit an individual from lifting the toe end of their foot towards their shin when walking. The sock is made of an elastomeric fabric 20 and is contoured to fit the foot, heel, ankle and calf. The sock is open at the toe-end 30. A shin portion 40 and an upper foot portion 50 of the sock comprise additional pre-stressed panels 60, 70 that act to inhibit motion of the foot portion away from the shin portion and act to provide an upward lifting of the foot portion of the sock towards the shin portion.

The sock of FIG. 1, while effective, may have a number of drawbacks for the wearer. The elastic material of the sock provides a tight fit and, thus, may be difficult for a wearer to put on. The problem of donning the sock is increased for wearers that have restricted use of, or control of, their hands, for example stroke victims. Furthermore, it may be difficult to locate the sock in the optimum position for supporting the foot and the effect of the pre-stressed panels may be diminished by frictional interaction between the sock and the leg.

Accordingly, it is an aim of the present invention to provide an improved orthotic support.

SUMMARY

The invention provides an orthotic sock as defined in the appended independent claims to which reference should now be made. Preferred or advantageous features of the invention are defined in dependent sub-claims.

Thus, in a first aspect the invention may provide an orthotic sock comprising a resilient material for conforming to a foot, ankle and a portion of the lower leg of a wearer. The sock further comprises means for restricting movement of the wearer's foot in one or more predetermined directions and/or assisting movement of the wearer's foot in one or more predetermined directions. Furthermore, an opening is defined through a posterior portion of the sock such that a portion of the wearer's calf may be exposed. The opening is a hole, having a length and a width, defined through a wall of the sock. Advantageously, the dimensions of the opening may be such that a user's foot can be passed through the opening.

The opening in the posterior portion of the sock preferably exposes a substantial portion of the wearer's calf muscle, particularly the lower portion of the calf muscle, when the sock is worn. Thus, it is preferable that the opening has a length of at least one half of a distance extending between a user's ankle joint and the top of the calf muscle, particularly preferably about two-thirds of this distance. It is preferred that the opening is ovoid, for example substantially oval or substantially elliptical. Particularly preferably with the length of the ovoid (running parallel to the length of the calf muscle, i.e. in a direction parallel to a line between heel and knee) being greater than the width of the ovoid (running perpendicular to the length of the calf muscle). In a preferred configuration the opening may be described as egg-shaped, having a narrower width towards the heel end of the opening and a greater width towards the knee end of the opening.

It is preferable that the width of the opening at its widest point is at least one half of the width of the user's calf muscle, preferably about two-thirds of the width of the user's calf muscle, or the entire width of the users calf muscle.

Different users will require different sizes of sock, and thus it is not possible to provide a precise numerical value for the length and width of the opening that will apply in all cases. It may be preferred, however, that the length of the opening will be between 5 cm and 30 cm for the majority of users, for example between 10 cm and 20 cm, and the width of the opening at its widest point will be between 5 cm and 20 cm for the majority of users, for example between 10 cm and 15 cm.

The opening defined through the posterior portion, which may be termed a cutaway portion, may provide a number of advantages.

The presence of the opening may advantageously allow a wearer to don the sock using only one hand. This one-handed donning of the sock may be particularly advantageous where the sock is used by somebody with impaired mobility in one arm or hand, for example if the orthotic sock is being used to treat a stroke victim. In this circumstance, the opening may allow the sock to be turned partially inside out so that only the foot segment is the right way round. The wearer can then insert his or her foot into the foot portion of the sock and snap a heel portion of the sock into place over his or her heel. The remainder of the sock may then be unrolled over the foot portion of the sock by placing the foot portion through the opening in the calf and pulling the calf section of the sock up over the leg. Alternatively, a user may place his foot through the leg opening of the sock, or partially through the leg opening of the sock, and out through the calf opening, in this case the calf opening may provide the user enough free room to hook the foot portion into place over his foot and then hoist the calf portion of the sock into position. Such one-handed donning of the sock may be near impossible without the presence of an opening in the posterior portion of the sock.

Even if the wearer has full use of two arms, the opening may make the act of donning the sock considerably easier than it would otherwise be.

The means for restricting movement of the user's foot in one or more predetermined directions may comprise a seam or a material panel that prevents movement of a users foot extending beyond a predetermined amount in a predetermined direction. This means may also be a means for assisting movement of the wearer's foot in one or more predetermined directions. In this case, the means may consist of a panel or panels of resilient material, or seams of resilient material, that act to bias the foot in a predetermined direction thereby assisting the wearer to move his or her foot in that predetermined direction.

The means for restricting movement of the user's foot may be a local variation in the properties of the fabric that forms the sock. For example, the fabric forming the sock may be a knitted fabric and the stitch properties may vary in type, number or density such that different regions of the material have different properties. Thus, it may be possible to form a sock from a single piece of fabric, but locally alter the properties of the fabric to restrict movement in a certain direction, or to assist or enhance movement in a certain direction. For example, it may be possible to knit a sock such that the majority of the sock is formed from a material that provides an even, multidirectional, stretching but the front portion of the sock has anisotropic stretching properties and acts to provide a dorsiflexional lift to the user's foot.

Preferably, the posterior opening is bounded by a perimeter, for example a hem or seam of material, and a portion of this perimeter acts to locate the sock at an upper portion of the calf muscle or gastrocnemius. The opening may allow the sock to be fixed or located over the calf muscle belly and thus may ensure location of the orthotic.

The orthotic support of the invention is particularly advantageous when used to assist dorsiflexion of a wearer's foot. Where the orthotic sock is designed to assist dorsiflexion, the sock comprises means for lifting the foot upwards or lifting the toes upwards towards the shin of the user, pivoting at the ankle joint. This movement is termed dorsiflexion. A dorsiflex sock may be advantageously used to treat patients having a neurological dysfunction which prevents the brain and central nervous system from initiating the foot lifting action (dorsiflexion). Such dysfunction may lead to the patient's toes dragging on the ground when they attempt to walk. Conditions in which a dorsiflex sock may be advantageously deployed include cerebral vascular accidents (commonly called strokes) and cerebral palsy. The sock could also be used for retraining a user to walk correctly following injury or following learnt misuse.

The use of an orthotic sock with a posterior opening or cutaway portion may advantageously increase the dynamic dorsiflexion moment produced by a dorsiflex assist sock.

The open back segment or opening in the back of the sock prevents resistance of the movement of resilient panels, which in this case would be dorsiflex assist panels (panels that bias the foot in such a way as to increase dorsiflexion). A sock that grips around the calf may resist the dorsiflexion movement due to frictional interaction between the muscle and the calf.

The lack of material over the calf of the wearer may also prevent an adverse stimulation of underlying muscles caused by shear of fabric over the calf, an increase in heat at the calf muscle and an increase in humidity at the calf muscle. Stimulation of calf muscles may cause the foot to be pulled downwards (i.e. contraction of the calf muscles causes the foot to point) which is the opposite reaction to dorsiflexion. Any stimulation of the calf muscle caused by the sock may act against the elastic pull of the sock's dorsiflexion assisting panels or seams. Advantageously, the opening or cutaway in the back of the sock may eliminate such stimulation of the calf muscle.

Furthermore, the lack of material in the calf portion of the sock may reduce pressure on the calf. Such pressure may additionally cause adverse stimulation of the calf muscle.

The opening in the back of the sock may assist the self-location of the sock. The open back allows the upper posterior portion of the sock to be located above the calf muscle belly. Furthermore, there is no tension between the heel portion of the sock and the upper posterior portion of the sock (because there is no material between the heel portion and the upper posterior portion) and the upper posterior portion of the sock is not pulled down. Thus, the opening or cutaway portion may advantageously assist the sock in maintaining its working location while being worn.

The close-fitting nature of the sock may increase the proprioception of the user this may be of advantage in patients whose normal sense of proprioception is diminished.

The sock may have an opening for the wearer's toes to project from. It is preferable in this situation, however, that the sock material extends forward to the sulcus. The sulcus is the groove or bend just forward of the main toe joints at the front of the foot. These joints can bend upwards. In a neurologically impaired patient the infantile reflex that lifts the whole foot up when the bottom of the foot is tickled may still be in place. The normal reaction to tickling of the foot is to push the toes and front of the foot downward thereby lifting the heel away from the stimulus. In neurological dysfunction the opposite occurs. In this group of patients failure of extending the sock forward to the sulcus can initiate the toes grasping downwards. Thus, the extension of the sock forward to the sulcus may advantageously reduce neurologically adverse reflexes in some groups of patients.

Where the orthotic sock is a sock for improving dorsiflexion of a user, the sock preferably comprises one or more panels of resilient material that extend down a shin portion of the sock to provide a dorsiflexion bias to the foot. Preferably these dorsiflexion assist panels extend around a circumference of an upper portion of the sock.

In further aspects the invention may provide an orthotic sock having a cutaway calf portion or an orthotic sock having a cutaway calf portion for allowing one-handed donning of the sock by a wearer. As described above, there are a number of advantages to the use of a cutaway calf portion in an orthotic sock.

In a further aspect the invention may provide an orthotic sock system comprising a sock as described above in combination with a sock lining. The lining may be in the form of a slip on or slipper of material, for example a nylon material. The lining may act to prevent abrasion between the patient's foot and the orthotic sock thereby reducing blisters on the patient's foot. The sock lining may also lower the friction of the patient's foot and thereby facilitate donning of the sock.

The specific techniques and structures employed to improve over the drawbacks of the prior devices and accomplish the advantages described herein will become apparent from the following detailed description of example embodiments and the appended drawings and claims.

DETAILED DESCRIPTION OF EXAMPLE EMBODIMENT

FIGS. 2a to 4b are schematic illustrations of an orthotic sock for assisting the dorsiflexion of a patient's foot. The sock (200) is constructed to conform to a wearer's foot, ankle and lower portion of the user's leg. Thus, the sock itself (200) may be described as having a foot portion (210) an ankle portion (220) a shin portion (230) and an upper portion (240). In use, the upper portion (240) of the sock encircles the wearer's leg just below the knee. Likewise the foot portion (210) ankle portion (220) and shin portion (230) conform to those regions of the wearer's body, as would be expected of a sock. The foot portion (210) defines an opening for the wearer's toes to extend through (250). In use, the material of the sock extends forwards of the wearer's sulcus.

The body of the sock is formed from a lightweight breathable elastomeric fabric, for example Lycra. Panels of the underlying Lycra elastomeric material (260) are stitched together at broad seams (320).

The sock further comprises a number of resilient dorsiflex assist panels (270, 280, 290, 300) sewn into the body of the sock over the top of the elastomeric material (260). The dorsiflex assist panels are formed from a resilient, breathable, material and are attached to an outer surface of the body of the sock by means of stitched seams (310).

Each of the dorsiflex assist panels provides a resilient pull on the foot of a wearer when the wearer flexes his foot. For example, when the wearer of the sock points his toes, the dorsiflex panels at the shin (270) and foot (300) are stretched. As the panels stretch they exert a force pulling the foot of the wearer upwardly towards the shin, pivoting around the heel. Thus the panels assist the dorsiflexion of the foot.

A shin dorsiflex assist panel (270) extends along the front portion of the sock and towards the upper portion (240) of the sock this dorsiflex assist panel extends circumferentially around the top of the sock.

The rear or posterior portion of the sock defines an opening or cutaway (400). The opening may be described as egg-shaped. This opening allows a wearer's calf to be exposed. The opening is bounded by a seam (405) and an upper portion of this seam (410) allows the sock to be fixed, anchored or located at the top of the calf muscle belly.

One important advantage that the sock may possess is that it can be put on one-handed. In order to put the sock on, the sock may be partially turned inside out so that the upper portion (240) is inside out but the foot portion (210) and ankle portion (220) are still the right way around. The foot can then be inserted into the foot portion (210) of the sock and the heel portion of the sock (220) pulled over the wearer's heel. The foot portion can then be passed through the opening in the sock and into the inverted calf section. The calf section of the sock can then be pulled up the leg until it is over the calf muscle bulk. The front top portion of the sock is then pulled upwards to make sure the top portion of the sock (240) is fully engaged with the leg and the upper portion of the calf opening (410) is located over the upper portion of the wearer's calf.

It is advantageous in use to use the sock in conjunction with a nylon slipper sock (not shown). This slipper sock or lining may be put on to a user's foot prior to donning the orthotic sock.

It is to be understood that this invention is not limited to the specific devices, methods, conditions, or parameters of the example embodiments described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "the" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the claimed invention has been shown and described in example forms, it will be apparent to those skilled in the art that many modifications, additions, and deletions can be made therein without departing from the spirit and scope of the invention as defined by the following claims.

What is claimed is:

1. An orthotic sock, comprising:
a resilient material for conforming to a foot, ankle and lower leg of a wearer, the sock further comprising means for restricting movement of the wearer's foot in one or more predetermined directions or assisting movement of the wearer's foot in one or more predetermined directions, wherein the means for restricting or assisting movement of the wearer's foot comprises one or more resilient panels incorporated into the sock including means for assisting dorsiflexion of the wearer's foot comprising a panel of resilient material that extends down a shin portion and a second panel of resilient material extending along an upper foot portion of the sock to assist the dorsiflexion of the wearer's foot, wherein a posterior opening is defined through a posterior leg portion of the sock the opening being defined such that the wearer's calf muscle belly is exposed through the posterior opening when the sock is worn so that the posterior opening allows the sock to be located over the calf muscle belly in order to ensure location of the orthotic, the opening being bounded by a perimeter, an upper portion of the perimeter acting to locate the sock at an upper portion of the calf muscle; and in that the panel extends around a circumference of an upper portion of the sock.

2. The sock according to claim 1, further comprising a toe opening formed therein through which toes of the wearer are allowed to project from the sock.

3. The sock according to claim 1, wherein the wearer's foot can be passed through the posterior opening in order to facilitate the process of donning the sock.

4. The sock according to claim 1, wherein the posterior opening is ovoid-shaped.

5. The sock according to claim 1, wherein the posterior opening increases a dynamic dorsiflexion moment of the sock.

6. The sock according to claim 1, wherein the posterior opening and resulting lack of material over the calf muscle belly eliminates adverse stimulation of the calf muscle.

7. The sock according to claim 1, wherein the posterior opening assists the sock in maintaining its working location while being worn.

8. An orthotic sock system comprising a sock according to claim 1 and a sock lining.

9. An orthotic sock, comprising:
a sock body made of a resilient material and including a foot portion, an ankle portion, and a leg portion configured to conform to a respective foot, ankle, and lower leg of a wearer, wherein the leg portion of the sock body includes a shin portion and an upper portion;
one or more panels made of a resilient material, incorporated into the sock body, and configured to assist dorsiflexion of the wearer's foot in one or more predetermined directions, wherein the one or more resilient panels includes a shin resilient panel that extends around a circumference of the upper portion of the sock body and down anterior portions of the upper portion and the shin portion of the sock body; and
a posterior opening defined through a posterior portion of the shin portion of the sock body and configured to receive and expose the wearer's calf muscle belly therethrough when the sock is worn in order to ensure location of the orthotic, wherein the posterior opening is bounded by a perimeter with an upper portion of the perimeter locating the sock body at an upper portion of the calf muscle, and wherein the opening is positioned below the shin resilient panel extending around the circumference of the upper portion of the sock body.

10. The sock according to claim 9, wherein the wearer's foot can be passed through the posterior opening in order to facilitate donning of the sock.

11. The sock according to claim 9, wherein the one or more panels made of a resilient material are attached over and to an outer surface of the sock body.

12. The sock according to claim 9, wherein the one or more panels made of a resilient material exert a resilient pull in the one or more predetermined directions on the foot of the wearer in response to the wearer flexing the foot.

13. The sock according to claim 9, wherein the shin resilient panel exerts a resilient pull in the one or more predetermined directions on the foot of the wearer in response to the wearer flexing the foot.

14. The sock according to claim 9, wherein the one or more panels made of a resilient material further include a foot resilient panel that extends across an upper portion of the foot portion of the sock body, wherein the shin resilient panel and the foot resilient panel are joined to the sock body at seams.

15. The sock according to claim 9, wherein the one or more panels made of a resilient material further include an ankle resilient panel that extends across an anterior portion of the ankle portion of the sock body, wherein the shin resilient panel and the ankle resilient panel are joined to the sock body at seams.

16. The sock according to claim 9, wherein the one or more panels made of a resilient material further include at least one lateral resilient panel that extends generally vertically along a lateral portion of the leg portion, the ankle portion, the foot portion, or a combination thereof, wherein the shin resilient panel and the lateral resilient panel are joined to the sock body at seams.

17. The sock according to claim 16, wherein the lateral resilient panel is positioned between the posterior opening and the anterior portion of the shin portion of the sock body.

18. The sock according to claim 9, wherein the one or more panels made of a resilient material further include a foot resilient panel that extends across an upper portion of the foot portion of the sock body, an ankle resilient panel that extends across an anterior portion of the ankle portion of the sock body, and a lateral resilient panel that extends generally vertically along a lateral portion of the leg portion, the ankle portion, and the foot portion, wherein the shin resilient panel, the lateral resilient panel, the ankle resilient panel, and the foot resilient panel are joined to the sock body at seams.

19. The sock according to claim 9, wherein the posterior opening is ovoid-shaped, wherein the posterior opening increases a dynamic dorsiflexion moment of the sock, wherein the posterior opening and resulting lack of material over the calf muscle belly eliminates adverse stimulation of the calf muscle, and wherein the posterior opening assists the sock in maintaining its working location while being worn.

20. An orthotic sock system comprising the sock according to claim 9 in combination with a sock lining.

* * * * *